(12) United States Patent
Karmon

(10) Patent No.: US 8,128,403 B2
(45) Date of Patent: Mar. 6, 2012

(54) DENTAL ABUTMENT FIXATED BY A NUT

(76) Inventor: Ben-Zion Karmon, Petach Tikva (IL)

( * ) Notice: Subject to any disclaimer, the term of this patent is extended or adjusted under 35 U.S.C. 154(b) by 535 days.

(21) Appl. No.: 12/049,430

(22) Filed: Mar. 17, 2008

(65) Prior Publication Data

US 2008/0227058 A1   Sep. 18, 2008

(30) Foreign Application Priority Data

Mar. 18, 2007 (IL) .......................... 181989

(51) Int. Cl.
*A61C 8/00* (2006.01)
(52) U.S. Cl. ..................... 433/174; 433/201.1
(58) Field of Classification Search .......... 433/173–176, 433/201.1, 172, 191–195
See application file for complete search history.

(56) References Cited

U.S. PATENT DOCUMENTS

| | | | | |
|---|---|---|---|---|
| 2,769,606 A * | 11/1956 | Larson | ............................ | 248/71 |
| 4,832,601 A * | 5/1989 | Linden | ......................... | 433/173 |
| 4,932,868 A * | 6/1990 | Linkow et al. | ................. | 433/174 |
| 5,049,073 A * | 9/1991 | Lauks | ........................... | 433/173 |
| 5,092,770 A * | 3/1992 | Zakula | .......................... | 433/172 |
| 5,116,225 A * | 5/1992 | Riera | ........................... | 433/173 |
| 5,413,480 A * | 5/1995 | Musikant et al. | ............. | 433/173 |
| 5,564,922 A * | 10/1996 | Rosa et al. | .................... | 433/173 |
| 5,658,146 A * | 8/1997 | Kisielewski et al. | ......... | 433/172 |
| 5,759,034 A * | 6/1998 | Daftary | .......................... | 433/173 |
| 5,989,024 A * | 11/1999 | Jonjic | .............................. | 433/76 |
| 5,989,028 A * | 11/1999 | Niznick | ......................... | 433/173 |
| 6,375,465 B1 * | 4/2002 | Engman et al. | ................ | 433/174 |
| 6,843,653 B2 * | 1/2005 | Carlton | .......................... | 433/174 |
| 6,939,135 B2 * | 9/2005 | Sapian | ........................... | 433/174 |

* cited by examiner

*Primary Examiner* — Cris L Rodriguez
*Assistant Examiner* — Hao D Mai
(74) *Attorney, Agent, or Firm* — Mark M. Friedman

(57) ABSTRACT

A dental abutment to be connected to a dental implant by a fixating nut, the fixating nut has a coronal end towards the oral cavity, an apical end towards the dental implant and internal thread between the coronal end of the fixating nut and the apical end of the fixating nut, the fixating nut being screwed over a screw having an external thread which matches the internal thread so the external thread can pass through the coronal end of the fixating nut.

25 Claims, 6 Drawing Sheets

FIG. 10
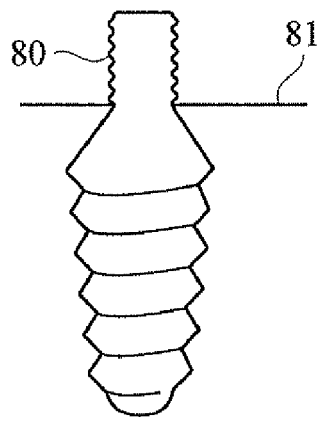
FIG. 12
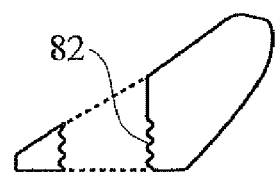
FIG. 11
FIG. 13
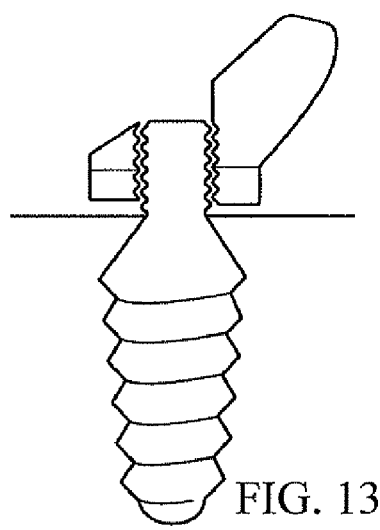
FIG. 8
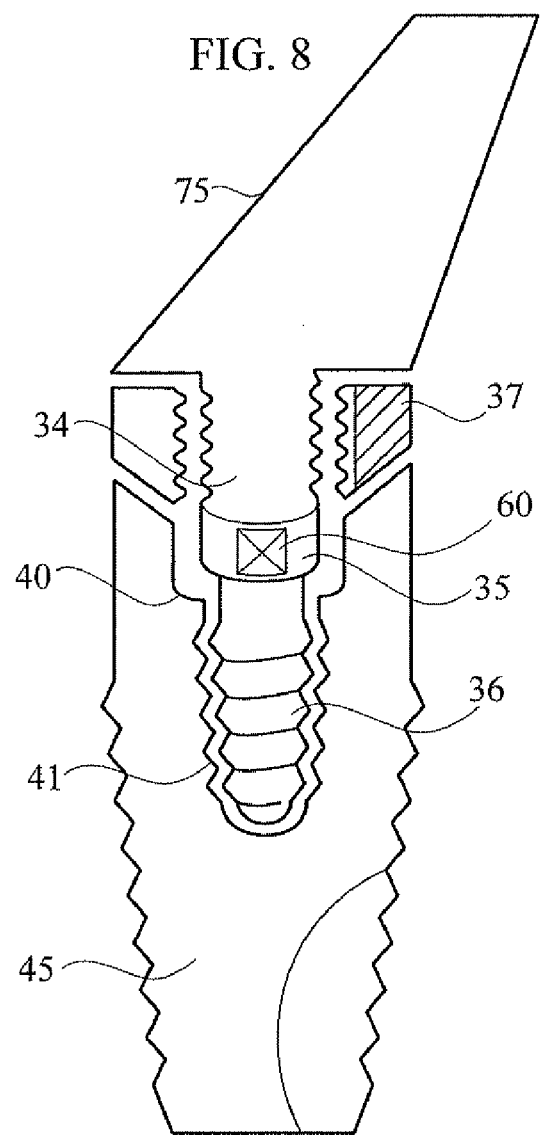

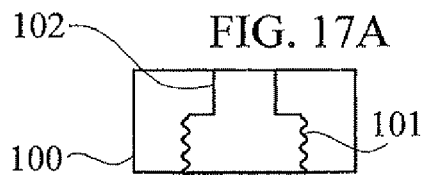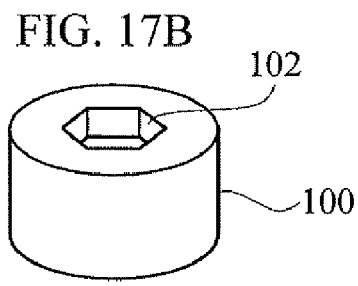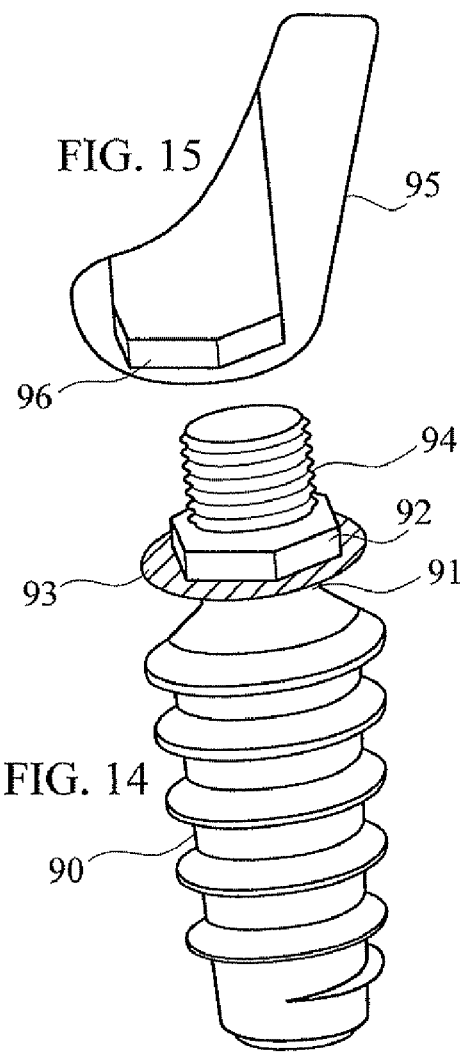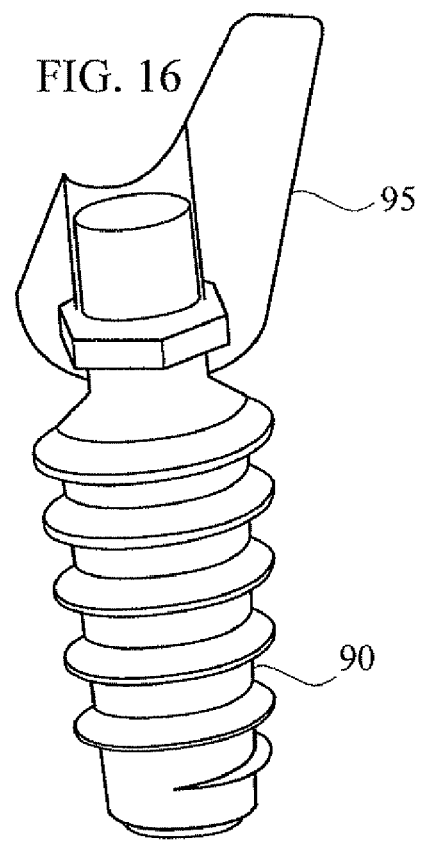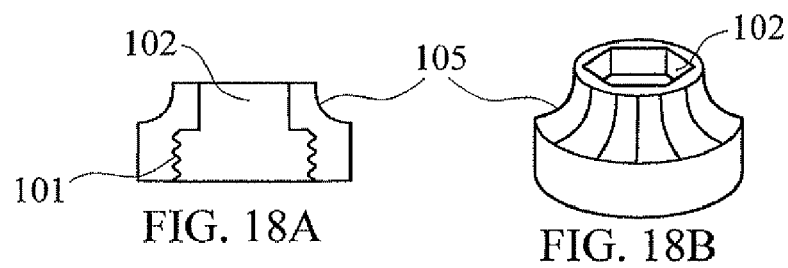

DENTAL ABUTMENT FIXATED BY A NUT

FIELD AND BACKGROUND OF THE INVENTION

In many cases of dental implants the implants are inserted in a non-parallel manner, due to bone architecture. Placing a denture over ball attachments which are connected to not parallel implants causes difficulties in the insertion and removal of the denture and causes damage to the ball and transfers damaging forces to the dental implants and the bone. In some cases the implant are located buccally or lingually to the desired location of the ball. Placing a regular ball attachment over misplaced implant is causing difficulties in the fabrication of the denture.

In regular implant cases for fixed restorations, where the implants are inserted in some angle to the desired angle of the prosthetic element, angulated abutments (1 in FIG. 1) are used. The regular angulated abutment 1 has an anti-rotational element usually an hexagonal 2 that engages a compatible anti-rotational element in the implant. The regular angulated abutment 1 has an opening 3 on the angulated wall 4 to allow the insertion of the fixating screw 5. This design is not suitable for ball attachment because the hole for the insertion of the screw prevents the producing of a full ball. A hole in an angulated abutment 1 still leaves enough walls for the retention of the prosthesis, but a partial ball can't function. Therefore the conventional ball attachment FIG. 2 has no anti-rotational element. Since the conventional ball attachment FIG. 2 has no anti-rotational element it can not be used as angulated ball attachment because the correct angle can not be determined by the doctor. One solution for this problem is to make the abutment from two parts, each part has an anti-rotational element FIG. 3. The first element 6 has a first anti rotational element 7 which is engaging the anti-rotational element of the implant and has an upper anti-rotational element 8. The second part 9 is in the shape of a plate and has an anti-rotational element 10 that engages the upper anti-rotational element 8 of the first part 6. The second part 9 has a ball 11 which is angled to the long axis of the dental implant. Both parts are fixated to the implant by a fixating screw 12. The presence of two parts increases the risk of screw loosening and the management by the doctor is more difficult. If the screw is loosened the connection between the ball part and the abutment part is not maintained and can lead to fracture of one of the parts. The main disadvantage of this solution is that the hole for the screw forces the ball to be angled to extreme angulations, which are very rare. The present application will describe several embodiments to allow angulated ball attachments without increasing the risk of screw loosening and to allow any angle of angulation. The following description will describe the embodiments for straight abutments, angulated abutments and angulated ball attachment for dental use. The same principles can be used for other dental abutments and for other orthopedic devices.

SUMMARY OF THE INVENTION

The present invention is describing a ball attachment which is placed such that its central long axis is displaced from the central long axis of the implant. The ball and the abutment element are forming one rigid unit that is stable even in case the fixating screw of the abutment is loosened. In some preferred embodiments the abutment element is at least partially inside the dental implant.

The angulated ball attachment allows having parallel balls in cases of not parallel implants and therefore allows easy insertion and removal of the denture by the patient.

Other objects and features of the present invention will become apparent in the following detailed description when taken in connection with the accompanying drawings which disclose one embodiment of the invention. It is to be understood that the drawings are designed for the purpose of illustration only and are not intended as a definition of the limits of the invention.

There are several embodiments of the device for angulated ball attachment.

Thus, according to the teachings of the present invention there is provided a device for connecting a ball to a bone implant comprising:

an abutment element and a ball, the abutment element is at least partially inserted inside the bone implant, the ball is rigidly connected to the abutment element so as to maintain their connection in case the connection of the abutment element to the bone implant is loosened, the ball is located such that the central long axis of the bone ball is displaced from central long axis of the bone implant.

According to a further feature of the present invention the angle between the central long axis of the bone implant and the central long axis of the ball is between 0 to 90 degrees.

According to a further feature of the present invention the angle is 15 to 45 degrees.

According to a further feature of the present invention the long axis of the ball is parallel the long axis of bone implant so the ball is displaced from the center of the bone implant.

According to a further feature of the present invention at least part of the ball is above the internal thread of the implant.

According to a further feature of the present invention the abutment element has an anti-rotational element to be engaged with an anti-rotational element of the bone implant.

According to a further feature of the present invention the anti-rotational element of the abutment element is in the shape of hexagon.

According to a further feature of the present invention the ball is located above one plane of the hexagon.

According to a further feature of the present invention the ball is located above one corner of the hexagon.

According to a further feature of the present invention the height of the abutment element is between 0.5 mm to 6 mm.

According to a further feature of the present invention the abutment element is angulated.

According to a further feature of the present invention the ball is located more displaced from the axis of the implant than the abutment element.

According to a further feature of the present invention the ball is located less displaced from the axis of the implant than the abutment element.

According to a further feature of the present invention the ball is soldered to the abutment element.

According to a further feature of the present invention the ball and the abutment element are one piece which is milled by a C.N.C machine.

According to a further feature of the present invention the ball and the abutment element are casted together.

According to a further feature of the present invention the ball is screwed to the abutment element.

According to a further feature of the present invention of claim the ball is glued to the abutment element.

According to a further feature of the present invention the abutment element is fixated by a screw to the bone implant.

According to a further feature of the present invention the abutment element is fixated by a rotating fixating nut to the bone implant.

According to a further feature of the present invention the abutment is fixated by friction to the bone implant.

According to a further feature of the present invention the ball is screw inside the abutment element.

According to a further feature of the present invention the screw has an internal element between the screw and the internal thread of the bone implant to prevent the loosening of the screw.

According to a further feature of the present invention the ball is replaced with another prosthetic connection.

There is also provided according to the teachings of the present invention a device for connecting to a dental implant comprising:

an abutment element and a fixating nut, the abutment element is connected to the dental implant, the fixating nut is connected to the dental implant so as to fixate the element abutment to the dental implant.

According to a further feature of the present invention the angle between the central long axis of the dental implant and the central long axis of the abutment element above the dental implant is between 0 to 90 degrees.

According to a further feature of the present invention the angle is 15 to 45 degrees.

According to a further feature of the present invention 3 the abutment element includes a ball attachment.

According to a further feature of the present invention the abutment element includes internal threads for receiving screwed restorations.

According to a further feature of the present invention the abutment element has an anti-rotational element to be engaged with an anti-rotational element of the dental implant.

According to a further feature of the present invention the anti-rotational element of the abutment element is in the shape of hexagon.

According to a further feature of the present invention the abutment element has internal threads to be screwed over external threads in the dental implant.

According to a further feature of the present invention the fixating nut is screwed over threads in the abutment element.

According to a further feature of the present invention the height of the abutment element is between 0.5 mm to 6 mm.

According to a further feature of the present invention the fixating nut is screwed over threads in the dental implant.

According to a further feature of the present invention the fixating nut is above the abutment element.

According to a further feature of the present invention the fixating nut is below the abutment element.

According to a further feature of the present invention the ball attachment is soldered to the abutment element.

According to a further feature of the present wherein the ball attachment and the abutment element are one piece which is milled by a C.N.C machine.

According to a further feature of the present invention the upper region of the fixating nut is narrower than lower region of the fixating nut.

According to a further feature of the present invention a ball attachment is screwed to the abutment element.

According to a further feature of the present invention the abutment element is fixated by a friction nut to the dental implant.

According to a further feature of the present invention 18 the abutment element include a screw which is screwed inside the dental implant and the screw has at least one flat surface.

According to a further feature of the present invention the upper region of the fixating nut is wider than the lower region of the fixating nut.

According to a further feature of the present invention the fixating nut is touching the head of the dental implant and the dental implant has internal threads.

According to a further feature of the present invention the fixating nut is placed inside the abutment element.

According to a further feature of the present invention the fixating nut includes an internal anti rotational element.

According to a further feature of the present invention the fixating nut includes an external anti-rotational element.

According to a further feature of the present invention the abutment element has two threads, one thread to be screwed inside the dental implant and second thread on which the fixating nut is screwed.

BRIEF DESCRIPTION OF THE DRAWINGS

FIG. 8 is a sectional view of a novel angulated attachment for cemented restoration, which is fixated to the implant with a fixating nut.

FIG. 10 is a sectional view of an implant with external threads.

FIG. 11 is a sectional view of an angulated abutment for cemented restoration which is screwed over the implant of FIG. 10.

FIG. 12 is a sectional view of the fixating nut for the angulated abutment of FIG. 11.

FIG. 13 is a sectional view illustrating the assembling of the nut of FIG. 12 below the angulated abutment of FIG. 11, which is connected to the implant of FIG. 10.

FIG. 14 is perspective view of an implant with external hexagon and external threads.

FIG. 15 illustrates an angulated abutment for the implant of FIG. 14.

FIG. 16 illustrates the angulated abutment of FIG. 15 on the implant of FIG. 14.

FIG. 17A is a sectional view of the fixating nut for fixating the angulated abutment of FIG. 15 to the implant of FIG. 14.

FIG. 17B is a perspective view of the fixating nut for fixating the angulated abutment of FIG. 15 to the implant of FIG. 14.

FIG. 18A is a sectional view of the fixating nut for fixating the angulated abutment of FIG. 15 to the implant of FIG. 14. The upper region of the nut becomes narrower.

FIG. 18B is a perspective view of the fixating nut for fixating the angulated abutment of FIG. 15 to the implant of FIG. 14. The upper region of the nut becomes narrower.

DESCRIPTION OF THE PREFERRED EMBODIMENTS

Figure 5:
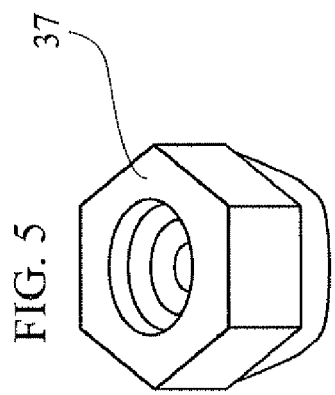
FIG. 5 is a perspective view of the fixating nut that fixate the angulated ball attachment screw of FIG. 4.
Figure 6:
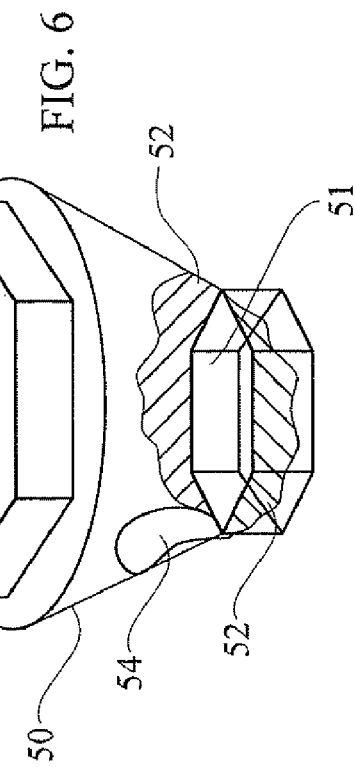
FIG. 6. is a perspective view of the rotating tool used to rotate the fixating nut of FIG. 5.
Figure 4:
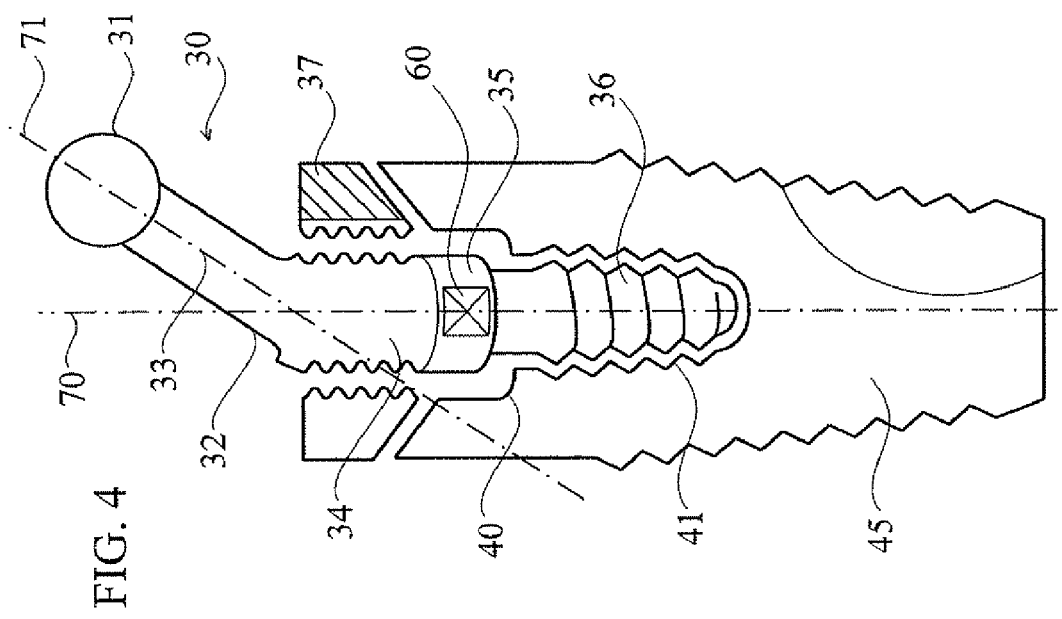
FIG. 4 is a sectional view of a novel angulated ball attachment which is fixated to the implant with a fixating nut.

In prior art solutions the location of the ball is limited by the opening for the fixating screw therefore allowing only large angled angulated ball attachments in which the ball is strongly displaced from the center of the implant. If the ball is too close to the central axis of the implant the fixating screw of the abutment can not be inserted. FIG. 4 is describing a sectional view of a novel angulated ball attachment screw 30. The ball 31 is rigidly connected to an angulated screw or bended crew 32 which is the abutment element. The angulated ball attachment screw 30 has preferably 5 sections. The ball 31, the neck 33 connected to the ball 31, an upper threaded region 34 below the neck 33 and with an angle in relation to the neck 33, an intra-hexagonal section 35 to be placed inside the internal hexagon 40 of the implant (for implants with internal hex) 45 and a lower threaded section 36 to be treaded to the internal thread of the implant 41. In one embodiment the angulated ball attachment screw 30 is screwed to the implant 45 until the ball 31 is in the right 3-dimensional position. Then a fixating nut 37 is rotated on the upper threaded region 34 until it engages the implant 45. Tightening the fixating nut 37 will lock the angulated ball attachment screw 30 in the desired position. The fixating nut 37 is placed over the angulated ball attachment screw 30 before connecting the ball attachment screw 30 to the implant 45. The fixating nut 37 has a rotating element to allow the rotation of the fixating nut 37. Preferably the outer surface of the fixating nut is in the shape of hexagon as can be seen in FIG. 5. For rotating the fixation nut 37 a special rotating tool is needed since the ball 31 is more displaced from the axis of the implant than the fixating nut 37 as can be seen in FIG. 4. FIG. 6 is describing the novel rotating tool 50. The rotating tool 50 has an internal hexagon 51 for receiving the outer hexagonal of the fixating nut of FIG. 5. In FIG. 6 the striated region 52 is just for illustrating purposes to illustrate the internal space of the rotating tool 50. The rotating tool is becoming wider above the internal hexagon 51 so the rotating tool 50 can rotate the fixating nut 37 of FIG. 5 without touching the ball 31. Preferably the outer wall of the rotating tool 50 has an opening 54 to allow easy insertion of the rotating tool 50 over the ball 31. The upper region 55 of the rotating tool 50 preferably has an anti-rotational configuration like a hex to allow its engagement with a rotating device like a ratchet.

Figure 7:
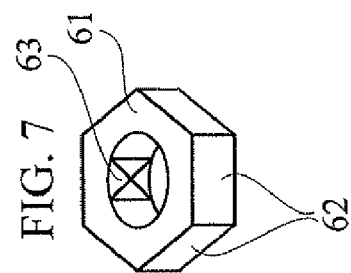
FIG. 7 is a perspective of a press nut that can fixate the angulated ball attachment screw of FIG. 4.

In another preferred embodiment the intra-hexagonal section 35 of the angulated ball attachment screw 30 has at least one region of straight plane 60 or any other anti-rotational element so after screwing the angulated ball attachment screw 30 inside the implant 45 a novel press nut 61 in FIG. 7 is inserted inside the internal hexagon 40 of the implant 45. The press nut 61 has an external hexagonal surface 62 to engage the internal hexagon 40 of the implant 45 and an internal straight plane 63 to engage the straight plane 60 of the angulated ball attachment screw 30. This press nut 61 prevents rotation of the angulated ball attachment screw 30 and in case the angulated ball attachment screw 30 was unscrewed it can be returned exactly to the previous location. In one embodiment the angulated ball attachment screw 30 is fixated only by the fixating nut 37 and for this embodiment the intra-hexagonal section 35 can be circular. In another embodiment the angulated ball attachment screw 30 can be fixated only by the press nut 61. In this embodiment the press nut 61 is preferably inserted with slight friction. In another preferred embodiment the angulated ball attachment screw 30 is fixated by both the fixating nut 37 and the press nut 61. The press nut 61 preferably is protruding slightly above the implant 45 to allow easy removal of the press nut 61.

In the embodiment of FIG. 4 the ball 31 can be located at least partially above the internal thread 41 of the implant 45. The long axis of the neck and the ball 71 is angulated to the long axis of the implant 70.

Figure 9:
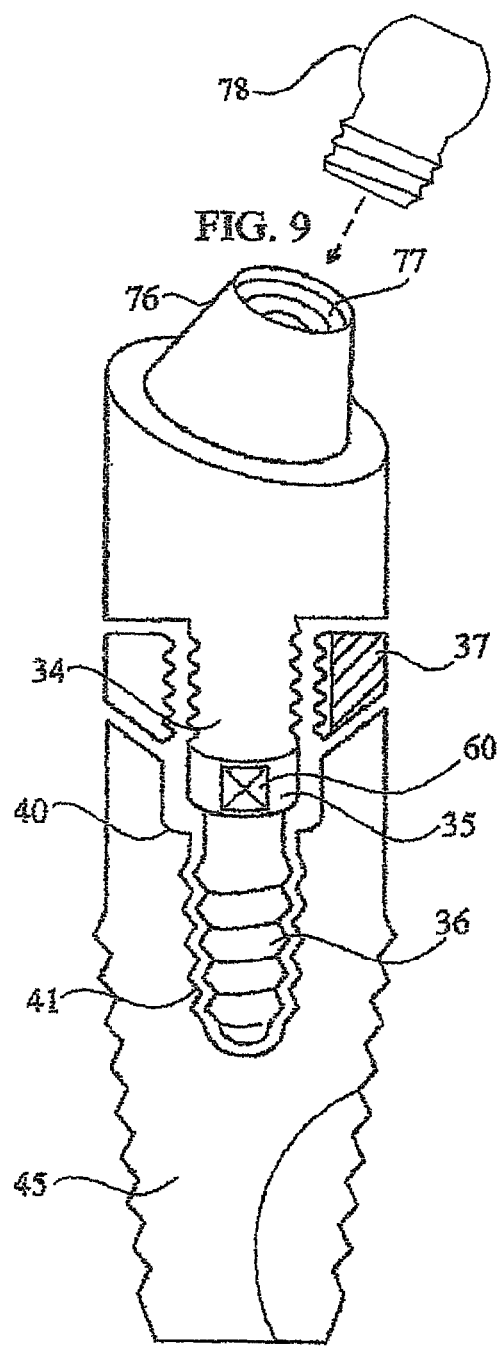
FIG. 9 is a sectional view of a novel angulated attachment for screwed restoration, which is fixated to the implant with a fixating nut.

The same principles can be used for other types of abutments. FIG. 8 illustrates the use of an angulated abutment for cemented restorations. The abutment 75 is rotated to the correct angulation and then the fixating nut 37 is fixating the abutment. In a preferred embodiment the abutment 75 includes an anti-rotational element like a hexagon on its external surface or an internal hole with an anti-rotational element. FIG. 9 illustrates the use of an angulated abutment 76 for screwed restorations. In this embodiment because there is no hole for the fixating screw the internal threads 77 can be placed in any angulation.

In these embodiments of FIGS. 4-9 not only the angle of the abutment can be controlled but also the height of the abutment. When the abutments are rotated their height in relation to the implant 45 is changed. The same principles can be used for straight abutment for cemented or screwed restorations. In these embodiments rotating the abutment is changing only the height of the abutment and the angulation is the same since these abutments are straight.

The control of the height of the straight and angulated abutment is very useful in the fitting of the restoration. In many cases of a restoration over large number of implants, the restorations, at the beginning, are not fully seated over the abutments, resulting in a lot of time and efforts spent by the dentist and the dental technician to achieve the correct fitting of the restoration to the abutments. Using the novel abutments of FIGS. 4-9, in which the abutments are fixated by nuts allows the dentist to change easily the position of the abutments to reach fitting to the restorations. This capability of changing the 3-dimensional position of the abutments is very important when using computerized systems for inserting the implants and immediately delivering the restorations that were prefabricated using C.N.C. systems. In many cases slight discrepancies between the prefabricated restorations and the abutments can be found, resulting in difficulties in seating the prefabricated restoration. The ability to slightly change the position of the abutments can solve this problem.

Figure 2:
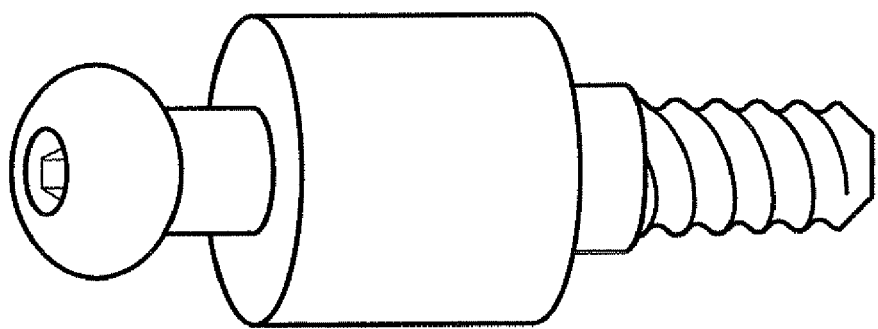
FIG. 2 is a perspective view of a conventional straight ball attachment.
Figure 1:
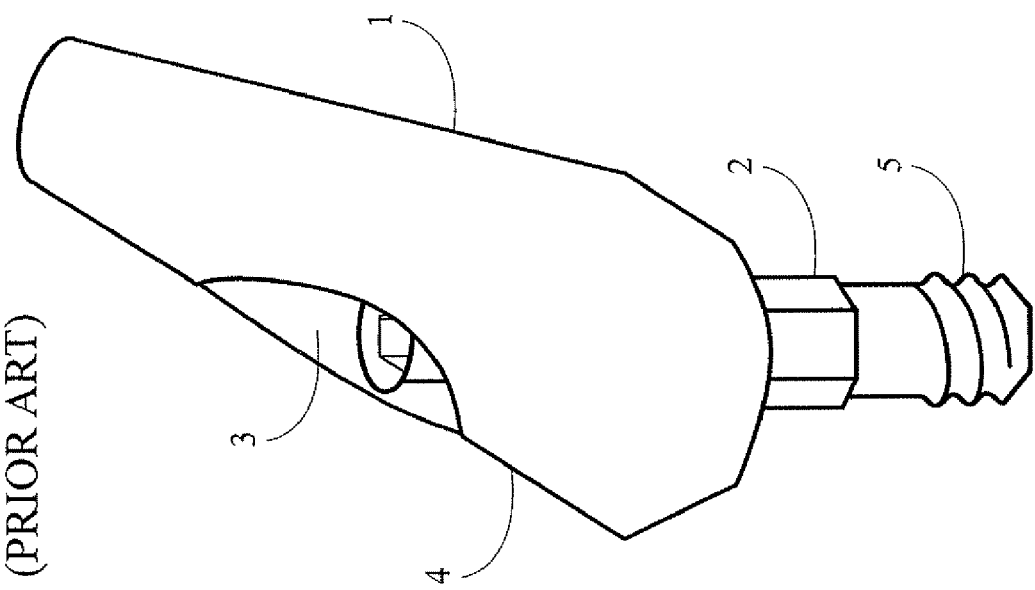
FIG. 1 is a perspective view of a conventional angulated abutment.
Figure 3:
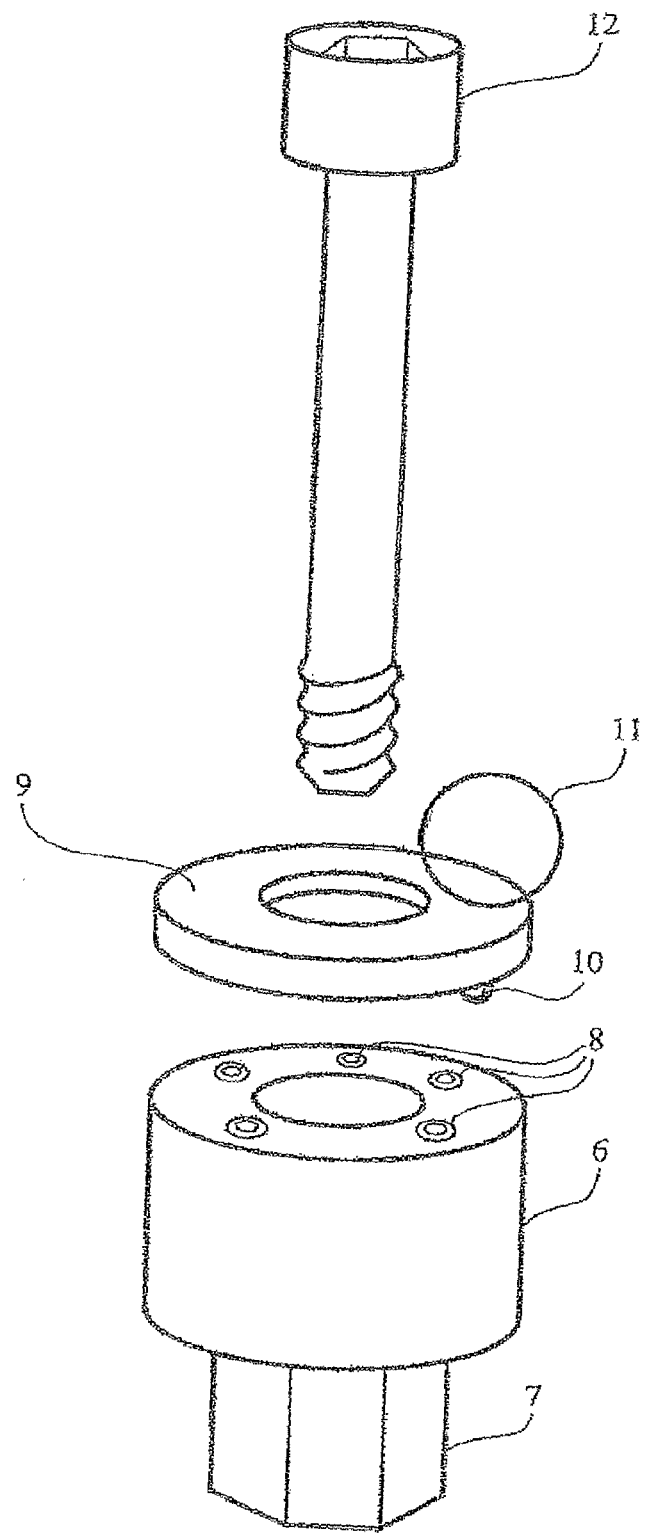
FIG. 3 is a perspective view of a prior art of two pieces angulated ball attachment with two anti-rotational elements.

Another advantage of the angled abutments for cemented restorations that are fixated by a nut instead of a screw is that there is no hole in the abutment (3 in FIG. 1) and therefore there is more surface for cementation resulting in improved retention. Moreover there is no need to deal with this hole when preparing and delivering the temporary and the final restorations.

In another preferred embodiment the use of fixating nut can be on a implant with external thread. When the implant is becoming narrow, especially in the coronal region of the implant it becomes impractical to have internal threads in the implant for the fixation of the abutments. In these cases the implant can be a one-piece implant that the dentist has to grind inside the mouth or the implant includes an external protrusion and the abutment is connected by friction. FIG. 10 illustrates a preferred embodiment of an implant having external threads 80 above the bone level 81. FIG. 11 illustrates a cross section of an angulated abutment having internal threads 82 that matches the external thread 80 of the implant of FIG. 10. Before placing the abutment of FIG. 11 on the implant of FIG. 10, a fixating nut is placed over the implant. FIG. 12 illustrates a cross section of the fixating nut. The external surface of the fixating nut is preferably in the shape of a hexagon as illustrated and explained above for FIG. 5 and the novel tool of FIG. 6 can be used for rotating the fixating nut. After placing the fixating nut of FIG. 12 over the implant of FIG. 10 the abutment of FIG. 11 is placed over the implant. When the desired 3-dimensional position of the abutment is reached the fixating nut is rotated counter-clockwise upwards till it is touching the abutment. After tightening the fixating nut the abutment is fixated. FIG. 13 illustrates the abutment and the fixating nut together on the implant. Tightening two nuts against each other is strongly fixating the nuts. The abutment of FIG. 11 has internal threads 82 and therefore behaves like a nut. The abutment of FIG. 11 preferably has an anti-rotational element to allow the use of a rotating tool for positioning the abutment over the implant. This anti-rotational element can be a hexagon on the external surface of the abutment of internal hexagon above the internal threads.

The implant of FIG. 10 is inserted by having two nuts with external hexagonal surfaces. When the two nuts are touching each other, rotating clockwise the upper nut will insert the implant and rotating counter clockwise of the lower nut will remove the implant. The two nut can have the same external diameter or to be different. After the insertion of the implant, the upper nut is removed and the abutment of FIG. 11 is attached as described above.

In another embodiment the abutment is fixated by a nut which is placed after the abutment. FIG. 14 illustrates an implant 90 with a narrow neck 91. Above the narrow neck there is an anti-rotational element like a hexagon 92. Preferably the lower region of the hexagon 93 is larger than the hexagon 92. Above the hexagon 92 there is an external thread 94 like the implant of FIG. 10. FIG. 15 illustrates an angulated abutment 95 with an internal hexagonal socket 96. The internal socket of the abutment is illustrated by dotted lines. The internal hexagonal socket 96 of the angulated abutment 95 is matching the hexagon 92 of the implant 90 in FIG. 14. The angulated abutment 95 is seated on the implant 90 so the hexagon 92 of the implant 90 is inside the socket 96 of the angulated abutment 95. FIG. 16 illustrates the abutment 95 seated over the implant 90. FIGS. 17A and B illustrates the nut 100 for fixating the angulated abutment 95 to the implant 90. The nut 100 has internal threads 101 that are matching the external threads 94 of the implant 90. The nut 100 has an internal anti-rotational element like a hexagon 102 above the internal threads 101. By using a rotating tool inside the hexagon 102 of the nut 100, the nut 100 is screwed over the external threads 94 of the implant and fixating the angulated abutment 95 to the implant. Because the implant 90 includes a hexagon 92 below the external threads 94 there 6 possible locations of the angulated abutment and impressions can be taken for preparing the abutments in the dental laboratory. In a preferred embodiment illustrated in FIGS. 18A-B, the upper region 105 of the nut 100 is becoming narrower so the nut 100 is not protruding outside the angulated abutment 95.

When the angulated abutment 95 is seated over the implant 90, the lower surface of the angulated abutment is touching the larger lower region 93 below the hexagon of the implant. This contact prevents passage of small molecules between the oral cavity to the bone through the abutment since it is very difficult to get complete sealing when placing the internal hexagon 96 of the angulated abutment 95 on the hexagon 92 of the implant.

In another preferred embodiment the hexagon 92 and the larger lower region 93 of the implant are also a nut or two separate nuts. In this preferred embodiment, the height of the hexagon can be changed and therefore the height of the abutments. This feature is useful to correct the position of the abutment in relation to the soft tissue and also to allow easy fitting of the restorations to the abutments as explained above.

Figure 20:
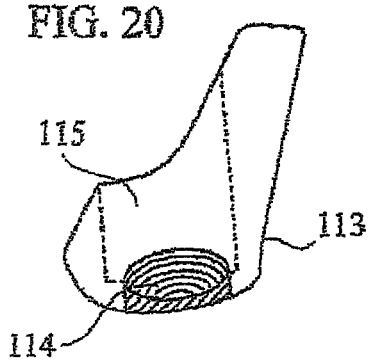
FIG. 20 illustrates an angulated abutment with internal threads and a space for fixating nut.
Figure 19:
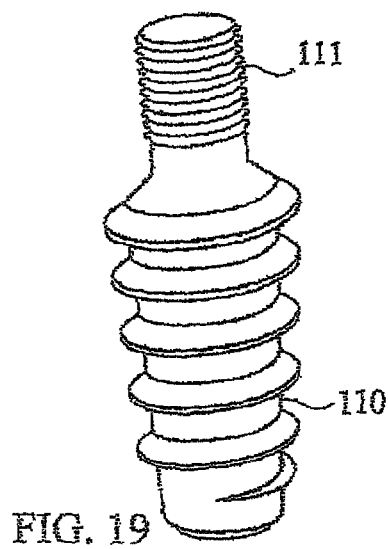
FIG. 19 is a perspective view of an implant with external thread.

In another preferred embodiment illustrated in FIG. 19 the implant 110 has external thread 111 and the angulated abutment 113 illustrated in FIG. 20 has an internal thread 114 that matches the external thread 111 of the implant 110. The angulated abutment 113 is screwed over the implant 110 to desired position and then the fixating nut 100 is screwed over the external threads 111 of the implant 110 inside a hole 115 in the angulated abutment 113 for fixating the angulated abutment 113 to the implant 110. In this embodiment almost any position of the abutment can be reached and the fixation is more convenient compared to the embodiments of FIG. 10-13. The diameter of the external thread 111 is 2.5-3.5 mm preferably 2.8-3.2 mm. The diameter of the fixating nut is 3.5-4.5 mm preferably 3.8-4.2 mm. The diameter of abutment is 4.5-5.5 mm preferably 4.8-5.2 mm.

It is clear that principles of the implants and abutments of FIGS. 10-20 are not only for angulated abutments but also for straight abutment, ball attachments and abutments for screwed restorations.

The description along the entire application was made for several dental abutments but the same principles can be used for any other type of dental abutments for implants or for orthopedic fixating devices.

In the described embodiments the abutment was connected to an internal hex in the implant. All the embodiments can be for other types of anti-rotational connections like external hexagon, spline, octagon etc.

What is claimed is:

1. A dental abutment device having a nut for connecting to a dental implant for supporting a dental prosthesis to treat human patients in need for dental restoration comprising:

a dental abutment element for supporting a dental prosthesis, a fixating nut and a dental implant, said dental implant has an internal thread, said dental abutment element includes an apical extension having an external thread, said external thread being screwed inside said internal thread of said dental implant, said fixating nut has a coronal end towards the oral cavity, an apical end towards said dental implant and internal thread between said coronal end of said fixating nut and said apical end of said fixating nut, said fixating nut being screwed over said apical extension so said apical extension pass through said coronal end of said fixating nut and through said apical end of said fixating nut, a largest diameter of said apical extension, apically to said fixating nut, being small enough to allow advancement of said fixating nut to its final location, apically to said dental abutment element, starting from an apical end of said apical extension.

2. A dental abutment device having a nut for connecting to a dental implant for supporting a dental prosthesis to treat human patients in need for dental restoration comprising:

a dental abutment element for supporting a dental prosthesis and a fixating nut, said dental implant has an internal thread, said dental abutment element includes an apical extension having an external thread, said external thread being screwed inside said internal thread of said dental implant, said fixating nut has a coronal end towards the oral cavity, an apical end towards said dental implant and internal thread between said coronal end of said fixating nut and said apical end of said fixating nut, said fixating nut being screwed over said apical extension so said apical extension pass through said coronal end of said fixating nut and through said apical end of said fixating nut, a largest diameter of said apical extension, apically to said fixating nut, being small enough to allow advancement of said fixating nut to its final location, apically to said dental abutment element, starting from an apical end of said apical extension, said dental implant has a coronal end and an apical end, an imaginary central long axis of said dental implant is extending between a center of said coronal end of said dental implant and a center of said apical end of said dental implant, said dental abutment element has a coronal end and an apical end, an imaginary central long axis of said dental abutment element is extending between a center of said coronal end of said dental abutment element and a center of said apical end of said dental abutment element, an angle between said imaginary central long axis of said dental implant and said imaginary central long axis of said dental abutment element is between 0 to 90 degrees.

3. The device of claim 2, wherein said angle is between 15 to 45 degrees.

4. The device of claim 3, wherein said dental abutment element includes a ball attachment.

5. The device of claim 3, wherein said dental abutment element includes internal threads for receiving screwed restorations.

6. The device of claim 1, wherein said apical extension has an anti-rotational element to be engaged with an anti-rotational element of said dental implant.

7. The device of claim 6, wherein said anti-rotational element of said apical extension is in the shape of hexagon.

8. The device of claim 2, wherein said apical extension has an additional external thread.

9. The device of claim 1, wherein the height of said dental abutment element is between 0.5 mm to 6 mm.

10. The device of claim 4, wherein said ball attachment is soldered to said dental abutment element.

11. The device of claim 4, wherein said ball attachment and said dental abutment element are undetachable one piece.

12. The device of claim 1, wherein said coronal end of said fixating nut is narrower than said apical end of said fixating nut.

13. The device of claim 1, wherein said dental abutment element is fixated by an additional friction nut to said dental implant.

14. The device of claim 13, wherein said apical extension has at least one flat lateral surface.

15. The device of claim 1, wherein said coronal end of said fixating nut is wider than said apical end of said fixating nut.

16. The device of claim 1, wherein said fixating nut is touching said dental implant.

17. The device of claim 1, wherein said fixating nut includes an external anti-rotational element.

18. The device of claim 2, wherein said dental abutment element and said apical extension are undetachable one piece.

19. The device of claim 4, wherein said ball attachment is displaced from said imaginary central long axis of said dental implant.

20. The device of claim 1, wherein an outer surface of said fixating nut is in the shape of a hexagon.

21. The device of claim 2, wherein said dental abutment element includes an anti-rotational element.

22. The device of claim 21, wherein said anti-rotational element is in the shape of a hexagon.

23. The device of claim 8, wherein said fixating nut is screwed over said additional external thread along said apical extension.

24. The device of claim 2, wherein said fixating nut includes an external anti-rotational element.

25. The device of claim 4, wherein a neck is located apically to said ball attachment, said neck is angulated to said apical extension.

* * * * *